(12) United States Patent
Kreiser

(10) Patent No.: US 8,081,812 B2
(45) Date of Patent: Dec. 20, 2011

(54) METHOD AND FACILITY FOR VISUALIZING AN OVERLAID PRESENTATION OF X-RAY IMAGES

(75) Inventor: Matthias Kreiser, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 459 days.

(21) Appl. No.: 12/383,982

(22) Filed: Mar. 31, 2009

(65) Prior Publication Data

US 2009/0257638 A1 Oct. 15, 2009

(30) Foreign Application Priority Data

Apr. 9, 2008 (DE) .......................... 10 2008 018 023

(51) Int. Cl.
*G06K 9/00* (2006.01)
(52) U.S. Cl. ........................................ 382/132; 382/130
(58) Field of Classification Search .................. 382/132, 382/130
See application file for complete search history.

(56) References Cited

U.S. PATENT DOCUMENTS

| | | | |
|---|---|---|---|
| 4,697,594 A * | 10/1987 | Mayo, Jr. ...................... | 600/443 |
| 5,376,801 A * | 12/1994 | Saotome et al. ........... | 250/482.1 |
| 6,501,826 B1 | 12/2002 | Kropfeld | |
| 7,236,622 B2 * | 6/2007 | Chen et al. ..................... | 382/132 |
| 7,778,453 B2 * | 8/2010 | Camus et al. .................. | 382/128 |
| 2004/0073111 A1 | 4/2004 | Poland et al. | |
| 2004/0167395 A1 | 8/2004 | Behrenbruch et al. | |
| 2005/0036668 A1 * | 2/2005 | McLennan et al. ........... | 382/128 |

FOREIGN PATENT DOCUMENTS

| | | |
|---|---|---|
| DE | 102006003126 A1 | 8/2007 |
| DE | 102006029718 A1 | 1/2008 |
| JP | 2006141534 A | 6/2006 |
| JP | 2007014483 A | 1/2007 |

OTHER PUBLICATIONS

Graeme Patrick Penney, "Registration of Tomographic Images to X-ray Projections for Use in Image Guided Interventions", Phd thesis, University College London, CISG, Division of Radiological Sciences, Guy's Hospital, King's College, London SE1 9RT England, 2000, pp. 1-13, 36-58 and 97-160.

* cited by examiner

Primary Examiner — Roy M Punnoose

(57) ABSTRACT

The invention relates to a method for visualizing an overlaid presentation of x-ray images. A first two-dimensional fluoroscopy image of an object of interest is provided. A second two-dimensional x-ray image of the object is intra-operatively recorded. A color is selected to a part of the first fluoroscopy image reproducing the object of interest. A complementary color corresponding to the selected color to the same part of the second fluoroscopy image reproducing the object is selected. The fluoroscopy images provided with the colors are overlaid. Deviations in the overlaid presentation remaining are identified with one of the added colors.

9 Claims, 8 Drawing Sheets

FIG 1  Prior Art
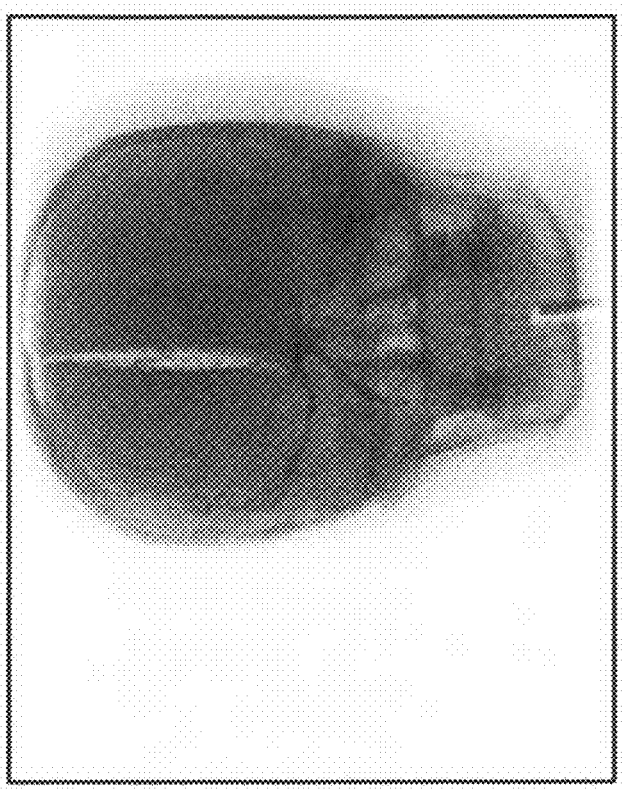
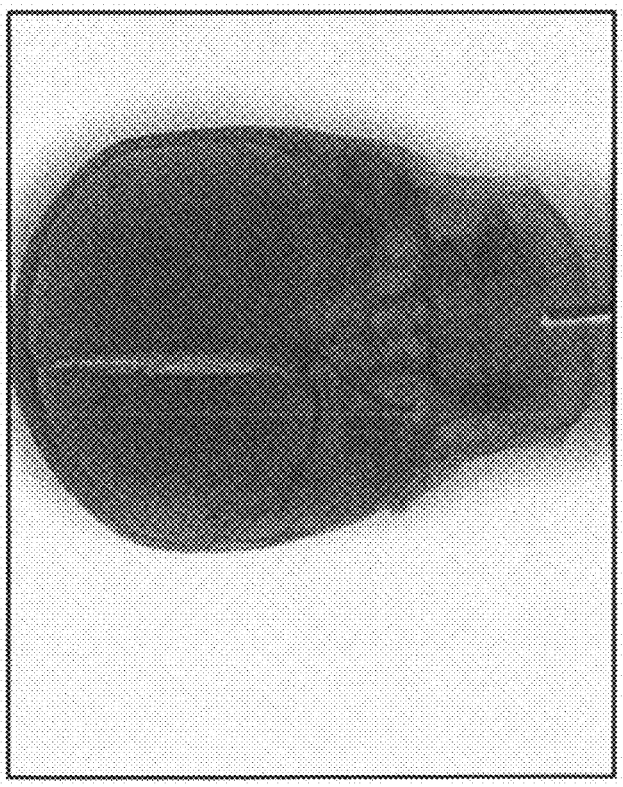
Left: IR1 (corresponds to a =0.0); Right: IF2 (corresponds to a =1.0)

$\alpha = 0.5$ : Equal parts of $I_{R1}$ and $I_{R2}$ are contained in the result image FIG 4
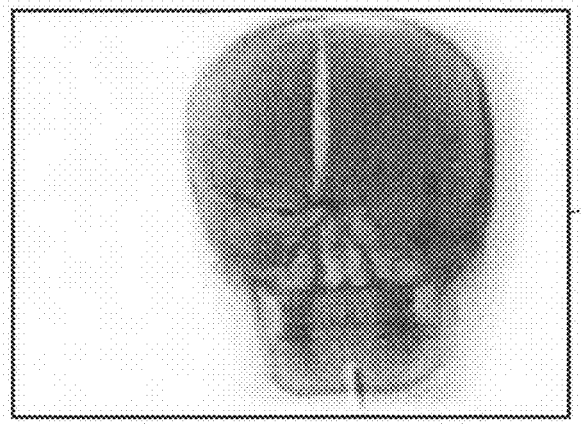
D
*
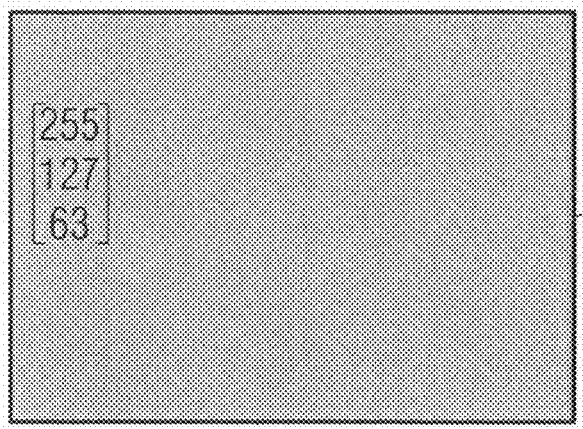
O
=
DO FIG 5
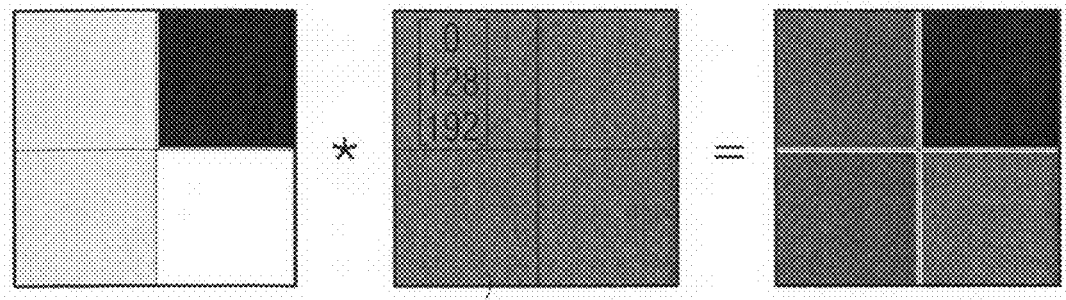
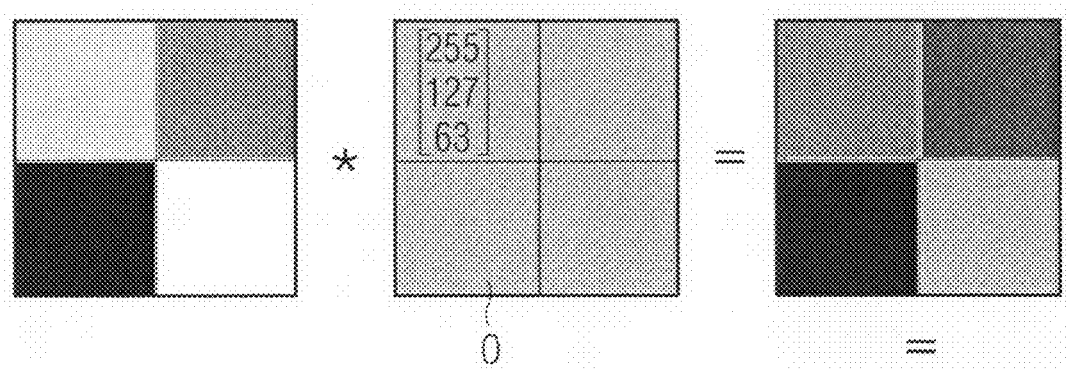

FIG 7
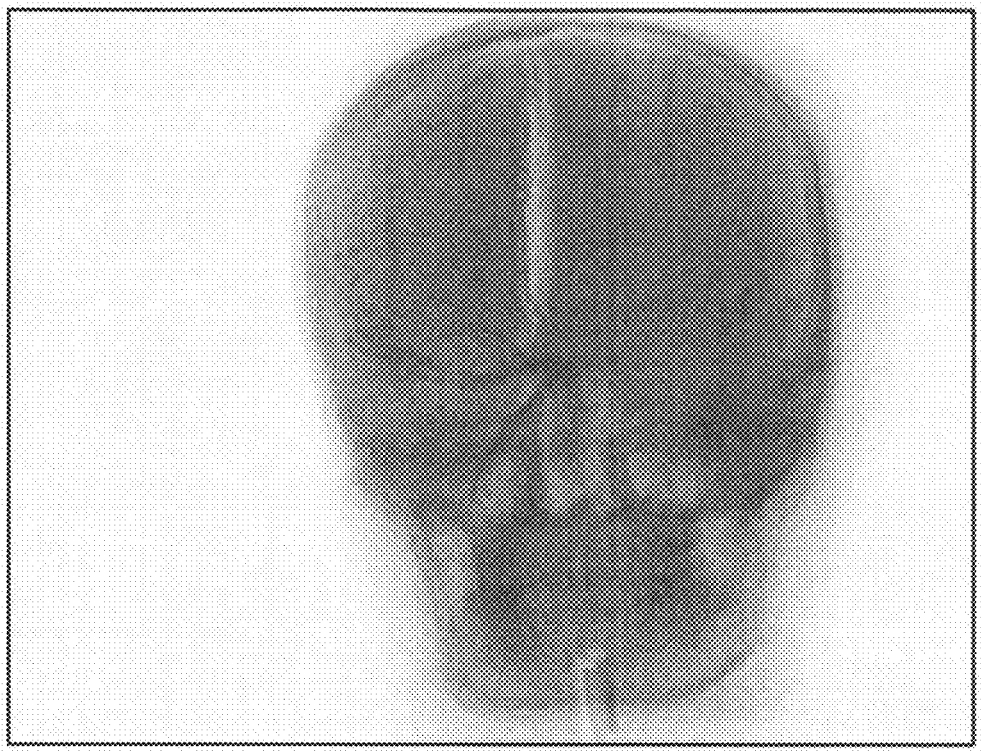
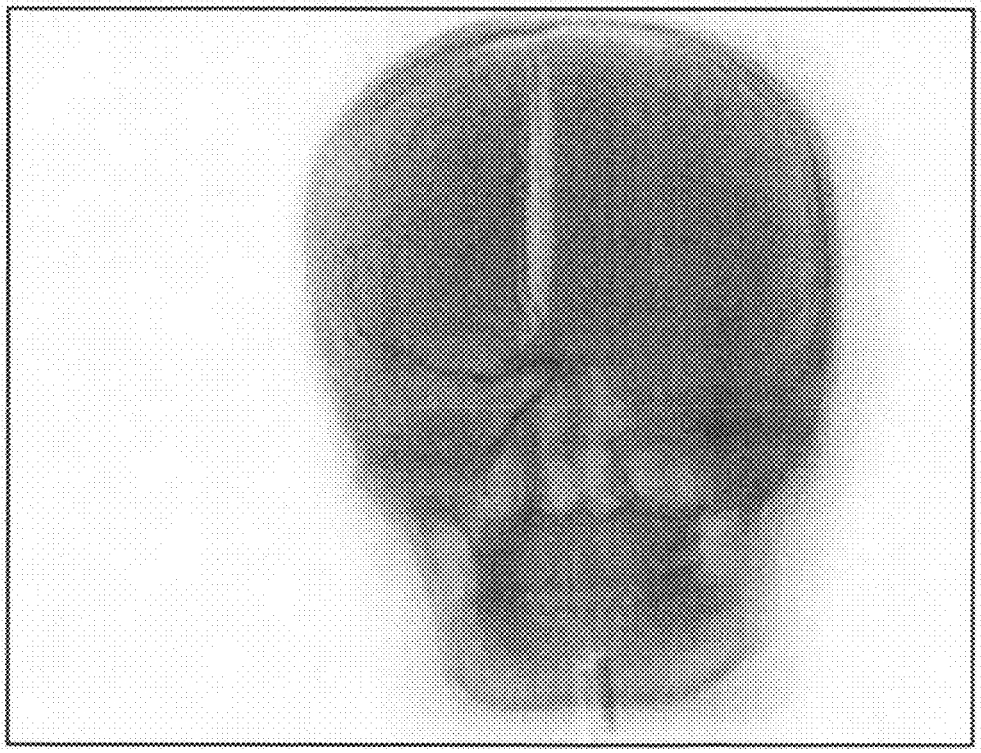

METHOD AND FACILITY FOR VISUALIZING AN OVERLAID PRESENTATION OF X-RAY IMAGES

CROSS REFERENCE TO RELATED APPLICATIONS

This application claims priority of German application No. 10 2008 018 023.8 filed Apr. 9, 2008, which is incorporated by reference herein in its entirety.

FIELD OF THE INVENTION

The invention relates to method and a facility for visualizing an overlaid presentation of x-ray images.

BACKGROUND OF THE INVENTION

The invention is applied for example in intra-operative imaging during a medical intervention. During a medical intervention real-time images (live images) are obtained for navigation of medical instruments e.g. with the aid of fluoroscopic imaging. Compared to 3D angio images, although these fluoroscopy images or 2D images do not show any spatial (3D) details, they are however available more quickly and minimize the exposure to radiation for patient and doctor. Ideally the spatial information is now retrieved by preoperative or intra-operative 3D images, obtained by CT, 3D angio, C-arm CT or MR images being registered with the two-dimensional images. The combination of co-registered 2D and 3D images now allows the doctor better orientation in the volume. This 2D/3D registration comprises two steps.

1. Image Registration:

It must first be determined from which direction a 3D volume must be projected so that it can be made to coincide with the 2D image. There are different approaches to this, which are described for example in "Graeme Patrick Penney, Registration of Tomographic Images to X-ray Projections for Use in Image Guided Interventions, Phd thesis, University College London, CISG, Division of Radiological Sciences, Guy's Hospital, King's College London, London SE1 9RT England, 2000, Pages 36 through 58 and 97 through 160".

2. Visualization

The second problem is the visualization of the registered images, i.e. the joint presentation of 2D image and projected 3D image. The standard method is the overlay, in which the two images are laid over one another based on different methods, as has already been proposed for example in the older patent application DE 10 2006 003 126.1.

Overlaying two x-ray images enables differences to be shown. Such differences can be transformations, i.e. the two x-ray images are displaced and/or rotated in relation to each other (which can frequently occur when a patient moves), but can also be anatomical changes such as introduced coils or stents for example. The visibility of these differences in the overlay, but also the ability of the differences to be allocated to the initial x-ray images, is greatly dependent on the visualization of the overlay.

One typical application is the 2D/3D fusion applications used in interventional radiology. These combine information from 3D data records with information from live recorded x-ray images (2D). This combination is only valid however provided the 3D data record is registered against the live x-ray image. This registration is invalid as a rule as soon as the patient has moved after the acquisition of the 3D data record. Then a 2D/3D re registration is necessary. To this end an artificial x-ray image (2D) is computed from the 3D data set and this is compared by overlaying with the live x-ray image. The transformation resulting from the patient movement (displacement and/or rotation) between the two images should be perceptible in the overlay. It is then possible to change the orientation of the 3D data record, so that the patient movement is compensated for and differences are no longer to be seen in the overlay. The 3D data record and the live-x-ray image are then correctly registered again.

The overlaying of two x-ray images is currently implemented by means of the Alpha blending method. In this method the two x-ray images $I_{R1}$ and $I_{R2}$ are combined with Alpha value $\alpha$ into a new image I:

$$I=(1-\alpha)*I_{R1}+\alpha*I_{R2}, \alpha\in[0,1] \tag{1}$$

Variation of the alpha value enables the proportion of x-ray images in the result image to be varied. For $\alpha=0.0$ only $I_{R1}$ is visible in the result image, for $\alpha=1.0$ only $I_{R2}$ and for $\alpha=0.5$ the same parts of both x-ray images are contained in the result image. An example for this visualization of the overlay is shown in FIG. 1.

SUMMARY OF THE INVENTION

The object of the invention is now to develop or embody a method or a facility so that the presentation of differences in at least two fluoroscopy images is improved.

This object is achieved by the features specified in the independent claims. Advantageous developments of the invention are specified in the dependent claims.

The subject matter of the invention is a method for visualizing an overlaid presentation of fluoroscopy images with the following steps:

a) Use of at least of one first two-dimensional fluoroscopy image of an object of interest,
b) Intra-operative recording of at least one second two-dimensional fluoroscopy image of the object,
c) Addition of a selected color to at least one part of the fluoroscopy image reproducing the object of interest,
d) Addition of a complementary color corresponding to a color selected in step c) to at least the same part of the fluoroscopy image reproducing the object of interest in accordance with step c),
e) Overlaid presentation of the fluoroscopy images provided with color in step c) and d), with
f) Deviations in the overlaying in accordance with step e) in the overlaid presentation remaining identified with one of the added colors.

Expediently in such cases identically overlaid image parts in the overlaying in accordance with step e) are identified in the overlaid presentation with a gray level.

Advantageously an added color or an added corresponding complementary color will be represented by a so-called RGB color value. The use of other color values or color spaces respectively is also conceivable.

Preferably the first fluoroscopy image used can be created from a preoperatively recorded three-dimensional data record.

The inventive method can be used in an advantageous manner for correction of a registration of the pre-operatively recorded three-dimensional data record with the fluoroscopy images recorded intra-operatively in step b).

Alternatively the fluoroscopy images from step a) and b) can be inverted before executing step c) to f).

A significant aspect of the invention lies in the use of colors for the overlaid presentation of x-ray images, i.e. the x-ray images (pure gray scale images) will be colored-in before being overlaid. In this case complementary colors can be used for coloring-in the x-ray images. The alpha blending described in equation (1), although applicable, is not ideal for the colored-in x-ray images. Therefore the equation (5) is used for combination of the two colored-in x-ray images. With these the two colored-in x-ray images can be overlaid with full intensity. The proportion of the two initial x-ray images in the result image can be varied as with alpha blending by means of an alpha value.

A further aspect of the invention is an imaging facility, embodied with modules for visualizing and overlaid presentation of fluoroscopy images in accordance with the steps of the previously explained method.

The inventive color visualization of the x-ray images enables differences between two x-ray images to be detected more easily. Furthermore the deviations or differences can be easily assigned to the initial x-ray images. A direct comparison between the inventive and the conventional process is shown in FIG. 7.

With the color visualized overlaying of x-ray images the previously-mentioned 2D/3D re-registration is easier to bring about. As soon as the overlaying of the artificial and of the live x-ray image produces a pure gray scale image, the patient movement is compensated for and the 3D data record and the live x-ray image are correctly registered again.

BRIEF DESCRIPTION OF THE DRAWINGS

An exemplary embodiment of the invention is described in more detail below with reference to a drawing.

The drawing shows the following figures:

FIG. 1 and FIG. 2 an overlaying of two x-ray images with the visualization in accordance with the prior art, FIG. 3 an example for complementary colors each identified with a respective RGB color value, FIG. 4 an example for a multiplication of an x-ray fluoroscopy image with one color, FIG. 5 a schematic illustration of the inventive color-visualized overlaying of x-ray images, FIG. 6 an overlaying of two colored-in x-ray images, FIG. 7 a diagram of a direct comparison of the visualization methods and FIG. 8 an imaging facility, preferably an x-ray diagnostic device for carrying out the inventive method.

DETAILED DESCRIPTION OF THE INVENTION

Figure 8:
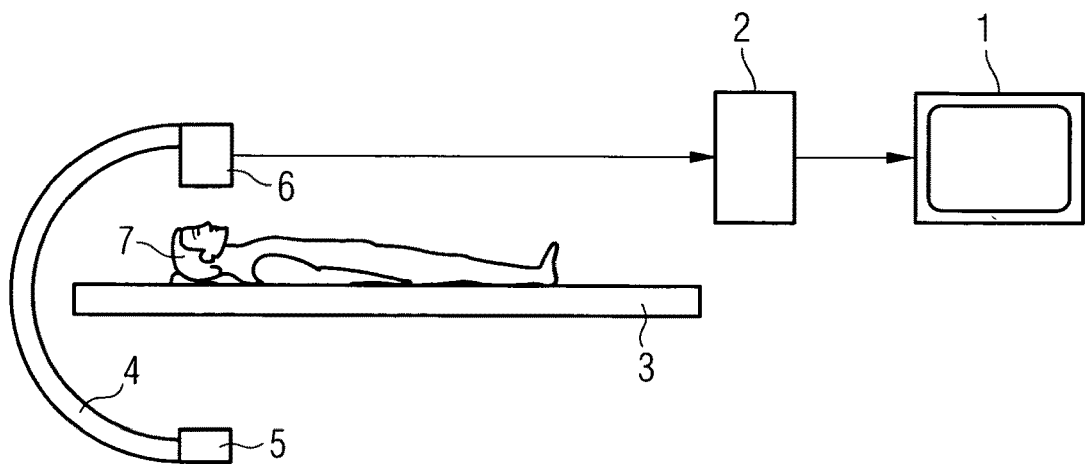

FIG. 8 shows an example of an x-ray diagnostic device which has a C-arm 4 supported rotatably on a stand not shown in the diagram, on the ends of which are accommodated an x-ray source 6, for example an x-ray emitter, and an x-ray detector 5.

The x-ray image detector 5 can be a rectangular or square flat semiconductor detector, which is preferably made of amorphous silicon (aSi).

Located the beam path of the x-ray source 6 is a patient support table 3 for receiving the head of a patient 7 to be examined for example. An imaging system 2, which receives and processes the image signals of x-ray image detector 5, is connected to the x-ray diagnostic device. The imaging signals to be processed can then be displayed on a display facility 1 connected to the imaging system 2.

The x-ray source 6 emits a ray bundle originating from a ray focus of the x-ray source 6 which hits the x-ray image detector 5.

The x-ray beam source 6 and the x-ray image detector 5 each circulate around the object so that the x-ray beam source 6 and the x-ray image detector 5 lie on opposite sides of the object.

To produce 3D data records the rotatably supported C-arm 4 with x-ray source and x-ray image detector 5 is rotated so that they rotate on a planetary track the x-ray beam source 6 as well as on a planetary track of the x-ray image detector 5 around an object to be examined (e.g. the head) of the patient 7. The planetary tracks can be followed partly or fully to create a 3D data record.

Figure 2:
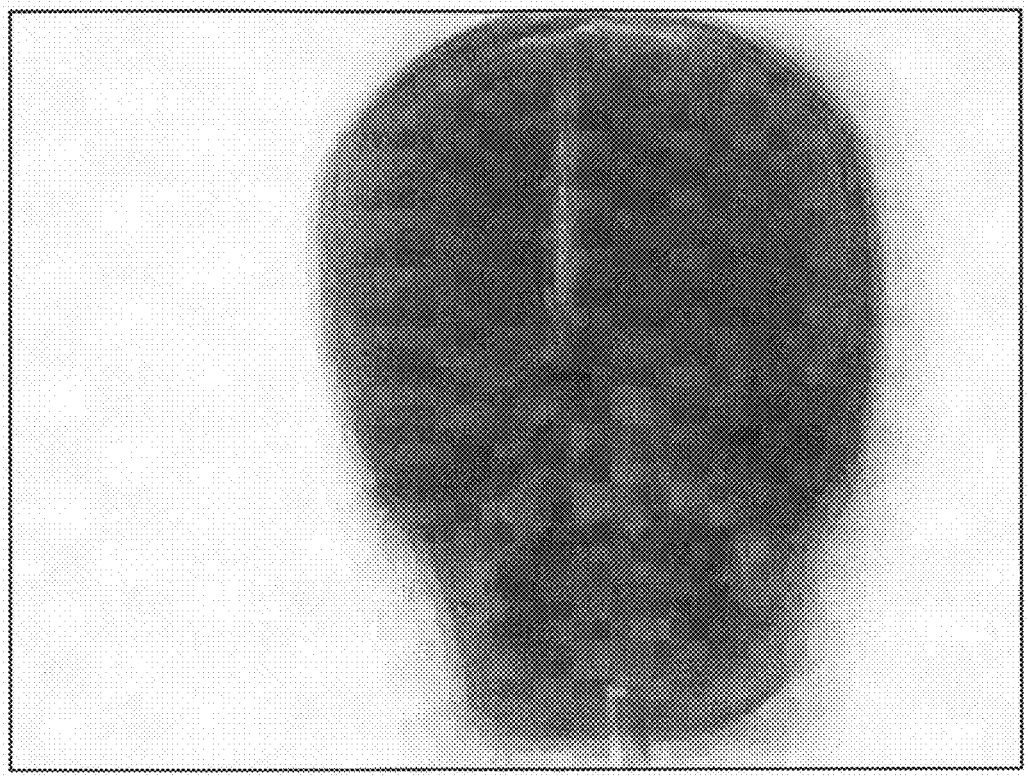

FIG. 1 and FIG. 2 reproduce a displacement of two x-ray images with the visualization in accordance with the prior art. In FIG. 1 the left-hand diagram shows an initial image $I_{R1}$ in accordance with $\alpha=0.0$ and the right-hand diagram an initial image $I_{R2}$ according to $\alpha=1.0$. in FIG. 2 corresponds to $\alpha=0.5$, which means that the same parts of $I_{R1}$ and $I_{R2}$ are contained in the result image.

Figure 3:
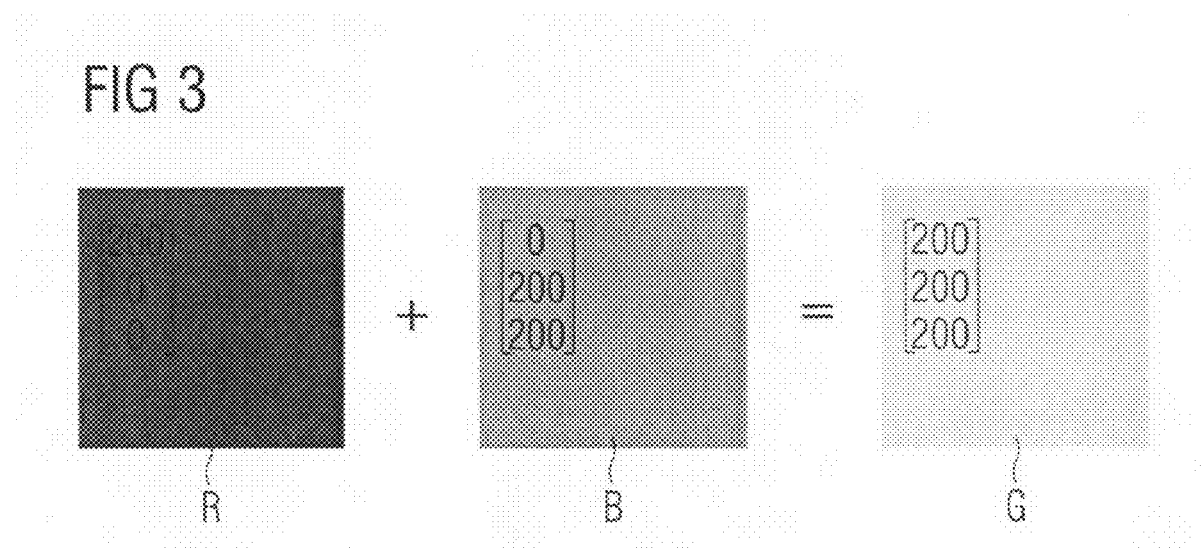

FIG. 3 shows an example of complementary colors identified by a respective RGB color, with the indicated vectors in the shown images specifying the RGB color value. Preferably the RGB color space is used in the application example. It is possible to use other color spaces or scales (e.g. CMYK etc.). In this case the first image is colored from the left with a red color tone R, the second image with a blue color tone B and the last image with grey tone G.

FIG. 4 shows an example for a multiplication of an x-ray fluoroscopy image with a color. In the figure the first image from the top is a fluoroscopy image D which is colored-in by a color O, also indicated by the shown vector, and from which as a result a colored-in image or an x-ray image DO to which the color O is added by multiplication is produced.

FIG. 5 shows a schematic illustration of an inventive color-visualized overlaying of x-ray images as follows:

Pixel left/top: The grey scale value of the pixel is identical in the initial images→The pixel in the result image has a gray tone.

Pixel right/top: The grey value in the lower original image is larger than in the upper image→The pixel in the result image has an orange color tone O.

Pixel left/bottom: The grey value in the upper original image is larger than in the lower image→The pixel in the result image has a cyan or blue color tone B.

Pixel right/bottom: The grey value of the pixel is identical in the original images→The pixel in the result image has a gray tone.

Figure 6:
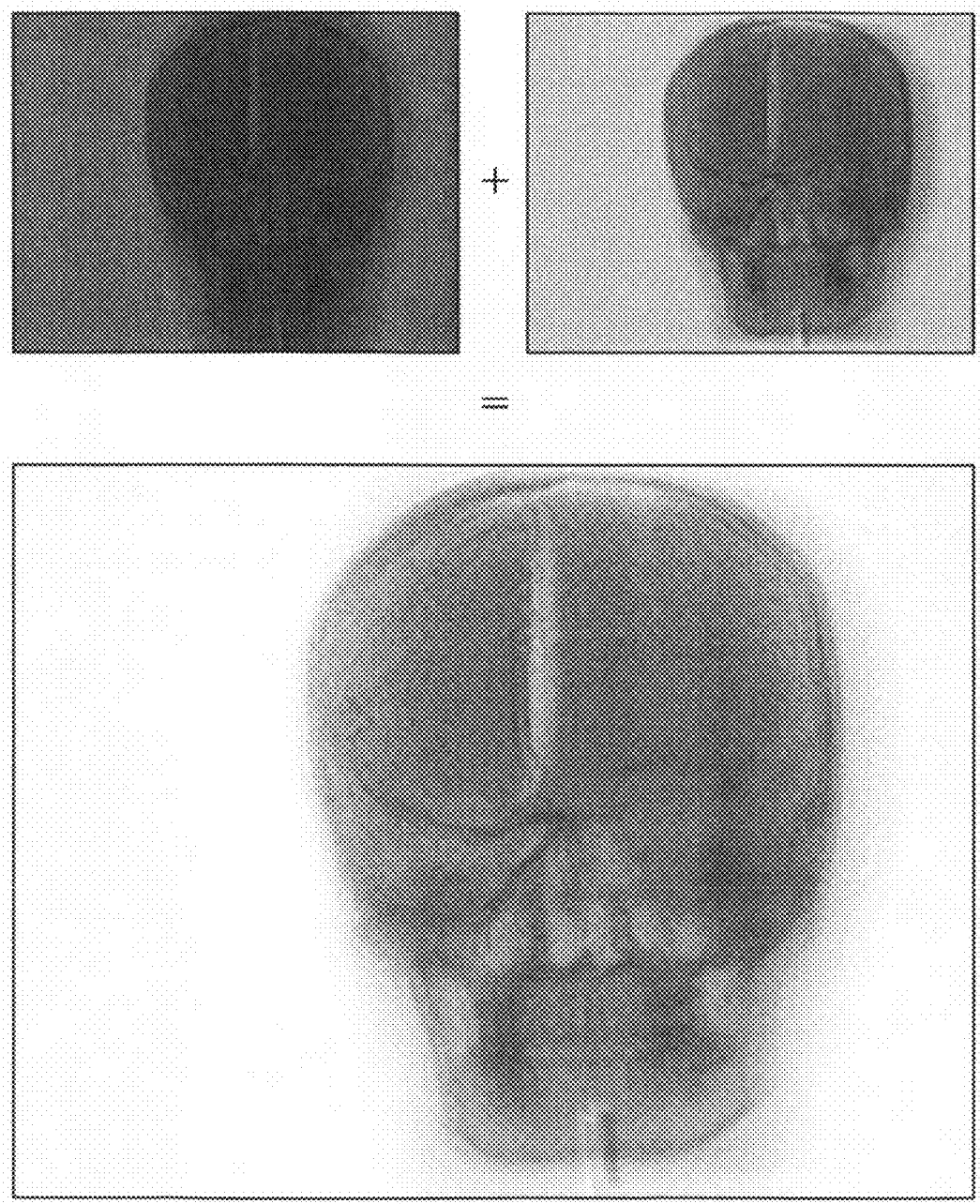

FIG. 6 shows an overlaying (result image below) of two colored-in x-ray images (image on the left colored-in with a blue color tone, image on the right colored in with an orange color tone).

FIG. 7 shows a presentation of a direct comparison of the visualization methods. As already mentioned above, the upper image shows the result of the conventional method and the lower image the result of the inventive method. In the lower image the differences or deviations are identified by the orange or blue coloring.

Normally x-ray images represent intensity values and are therefore pure gray scale images. The following equation then applies for the RGB color values in an x-ray image:

$$R=G=B, R, G, B \in [0,1] \qquad (2)$$

Each color channel according to the equation (2) contains the same information. It is therefore useful, to color-in x-ray images with complementary colors before overlaying them and to overlay said images instead of the pure gray scale images. Complementary colors are colors which produce a gray value when mixed. FIG. 3 shows a corresponding example. The x-ray images are colored in by multiplication with the selected complementary colors $\vec{c}_1$ and $\vec{c}_2$ (see FIG. 4):

$$C_{R1} = \vec{c}_1 * I_{R1}$$

$$C_{R2} = \vec{c}_2 * I_{R2} \qquad (3)$$

In such cases no information gets lost in the x-ray image, since in accordance with the equation (2) each color channel contains the same information. For the two complementary colors $\vec{c}_1$ and $\vec{c}_2$ the following equation applies:

$$\vec{c}_1 + \vec{c}_2 = \begin{pmatrix} x \\ x \\ x \end{pmatrix}, x \in [0, 1] \quad (4)$$

If the colored-in x-ray images $C_{R1}$ and $C_{R2}$ are now combined by addition, the following characteristics are produced for the resulting image:

Corresponding pixels in the x-ray image with identical gray values become gray again in the overlaid image.

Corresponding pixels in the x-ray image with different gray values become colored in the overlaid image. The color tone is determined by the pixel with the larger gray value.

A schematic illustration of these two characteristics is shown in FIG. 5. The following knowledge emerges from the two characteristics:

The overlaying of two identical x-ray images produced a gray scale image.

Differences in the overlaying of two non identical x-ray images are identified by colors and can be assigned to the x-ray image by the color tone (see FIG. 6).

If the proportion of the colored-in x-ray images $C_{R1}$ and $C_{R2}$ is to be varied in the result image, the equation (1) can be used for this purpose. However the intensity in the result image then becomes lower than necessary. For example the intensity for $\alpha=0.5$ is halved. Therefore the following formula is used for the combination I of the colored-in x-ray images $C_{R1}$ and $C_{R2}$:

$$I = \begin{cases} C_{R1} + 2\alpha * C_{R2} & \text{for } 0 \le \alpha < 0.5 \\ 2(1-\alpha) * C_{R1} + C_{R2} & \text{for } 0.5 \le \alpha \le 1.0 \end{cases} \quad (5)$$

For $\alpha=0.5$ $C_{R1}$ and $C_{R2}$ are simply added. For $\alpha<0.5$ $C_{R1}$ is completely contained in the result image and $C_{R2}$ is added into it in accordance with the Alpha value. And for $\alpha \ge 0.5$ $C_{R2}$ is completely contained in the result image and $C_{R1}$ is added in according to the alpha value.

Since structures (e.g. bones or blood vessels filled with contrast media) in x-ray images are identified by dark areas, the x-ray images can also be inverted prior to being colored in.

Within the framework of the invention the tomographic imaging apparatus involved can be a C-arm x-ray system, biplanar x-ray devices, computer tomographs, MR or PET. The C-arm 4 can also be replaced by a so-called electronic C-arm, in which x-ray source and x-ray image detector 5 are coupled electronically. The C-arm can also be guided on robotic arms which are accommodated on ceiling or floor. The method can also be executed with x-ray devices in which the individual image-creation components 5 and 6 are respectively held by a robot arm which is arranged on the ceiling and/or floor.

The invention claimed is:

1. A method for visualizing an overlaid presentation of an x-ray image of an object, comprising:

providing a first two-dimensional x-ray image of the object;

intra-operatively recording a second two-dimensional x-ray image of the object;

selecting a first color to a part of the first x-ray image reproducing the object;

adding the first color to the first x-ray image;

selecting a complementary color corresponding to the first color to an identical part of the second x-ray image reproducing the object;

adding the complementary color to the second x-ray image;

overlaying the first x-ray image with the second x-ray image to generate the overlaid presentation of the x-ray image; and identifying a deviation in the overlaid presentation of the x-ray image with one of the first color and the complementary color.

2. The method as claimed in claim 1, wherein an identically overlaid image part in the overlaid presentation of the x-ray image is identified with a gray level.

3. The method as claimed in claim 1, wherein the first added color is represented by a RGB color value.

4. The method as claimed in claim 1, wherein the complementary added color is represented by a RGB color value.

5. The method as claimed in claim 1, wherein the first x-ray image is generated from a pre-operative three-dimensional data set.

6. The method as claimed in claim 5, wherein the pre-operative three-dimensional data set is registered with the second x-ray image.

7. The method as claimed in claim 1, wherein the first and the second x-ray images are inverted before adding the first and the complementary colors.

8. The method as claimed in claim 1, wherein the overlaid presentation is represented by the following formula:

$$I = \begin{cases} C_{R1} + 2\alpha * C_{R2} & \text{for } 0 \le \alpha < 0.5 \\ 2(1-\alpha) * C_{R1} + C_{R2} & \text{for } 0.5 \le \alpha \le 1.0 \end{cases}$$

wherein:

$C_{R1}$ is the first x-ray image added with the first color, $C_{R2}$ is the second x-ray image added with the complementary color, I is the overlaid presentation.

9. An imaging apparatus for visualizing an overlaid presentation of an x-ray image of an object, comprising:

an x-ray source that emits x-ray beams;

an x-ray detector that records a second two-dimensional x-ray image of the object by detecting the x-ray beams; and an image processing unit that:

receives a first two-dimensional x-ray image of the object, selects a first color to a part of the first x-ray image reproducing the object, adds the first color to the first x-ray image, selects a complementary color corresponding to the first color to an identical part of the second x-ray image reproducing the object, adds the complementary color to the second x-ray image, and overlays the first x-ray image with the second x-ray image to generate the overlaid presentation of the x-ray image that identifies a deviation with one of the first color and the complementary color.

* * * * *